(12) United States Patent
Lamoise (10) Patent No.: US 10,709,503 B2
(45) Date of Patent: Jul. 14, 2020

(54) PROTECTIVE SLEEVE FOR A DERMATOLOGICAL TREATMENT DEVICE

(71) Applicant: URGO RECHERCHE INNOVATION ET DEVELOPPEMENT, Chenôve (FR)

(72) Inventor: Michel Lamoise, Bessey les Citeaux (FR)

(73) Assignee: URGO RECHERCHE INNOVATION DEVELOPMENT, Chenôve (FR)

(*) Notice: Subject to any disclaimer, the term of this patent is extended or adjusted under 35 U.S.C. 154(b) by 62 days.

(21) Appl. No.: 16/068,156

(22) PCT Filed: Jan. 6, 2017

(86) PCT No.: PCT/EP2017/000012
§ 371 (c)(1),
(2) Date: Jul. 5, 2018

(87) PCT Pub. No.: WO2017/118605
PCT Pub. Date: Jul. 13, 2017

(65) Prior Publication Data
US 2019/0015154 A1 Jan. 17, 2019

(30) Foreign Application Priority Data

Jan. 7, 2016 (FR) ...................................... 16/00034

(51) Int. Cl.
*A61B 18/20* (2006.01)
*A61N 5/06* (2006.01)
(Continued)

(52) U.S. Cl.
CPC ............ *A61B 18/203* (2013.01); *A61B 18/20* (2013.01); *A61B 50/00* (2016.02); *A61N 5/0616* (2013.01);
(Continued)

(58) Field of Classification Search
CPC ....... A61B 18/203; A61B 18/20; A61B 50/00; A61B 2560/0406
(Continued)

(56) References Cited

U.S. PATENT DOCUMENTS 5,514,126 A * 5/1996 Prescott ................. A61B 18/22
606/10
2012/0232539 A1* 9/2012 Liu ...................... A61N 5/0616
606/9

FOREIGN PATENT DOCUMENTS

WO 9952595 A1 10/1999

OTHER PUBLICATIONS

International Search Report in corresponding International Patent Application No. PCT/EP2017/000012, dated Mar. 28, 2017. 2 pages.

* cited by examiner

*Primary Examiner* — Amanda K Hulbert
*Assistant Examiner* — Philip C Edwards
(74) *Attorney, Agent, or Firm* — Leason Ellis LLP (57) ABSTRACT

Disclosed is a protective sleeve (1) for a dermatological treatment device comprising a laser head for firing a laser beam. The sleeve (1) comprises: a rigid shell (2) which is shaped such that it can be placed over the laser head and has a window (4) that can be positioned opposite the laser beam; a contact wall (5) arranged around the window (4) for contacting an area around a target area; and a means for attachment to the device, the attachment means being positioned as close as possible to the contact wall (5).

17 Claims, 5 Drawing Sheets

(51) Int. Cl.
*A61B 50/00* (2016.01)
*A61B 18/00* (2006.01)
*A61N 5/067* (2006.01)

(52) U.S. Cl.
CPC ............... *A61B 2018/00005* (2013.01); *A61B 2018/0047* (2013.01); *A61B 2018/0091* (2013.01); *A61B 2560/0406* (2013.01); *A61N 2005/067* (2013.01); *A61N 2005/0644* (2013.01)

(58) Field of Classification Search
USPC .......................................................... 606/9
See application file for complete search history.

PROTECTIVE SLEEVE FOR A DERMATOLOGICAL TREATMENT DEVICE

CROSS-REFERENCE TO RELATED PATENT APPLICATIONS

This application is a U.S. National Stage Application under 35 U.S.C. § 371 of International Patent Application No. PCT/EP2017/000012, filed Jan. 6, 2017, which claims the benefit of priority under 35 U.S.C. Section 119(e) of French Patent Application number FR 16/00034 filed Jan. 7, 2016, both of which are incorporated by reference in their entireties. The International Application was published on Jul. 13, 2017, as International Publication No. WO 2017/118605 A1.

The present patent application claims the priority of French patent application FR 16/00034 filed on Jan. 7, 2016, which is incorporated into the present patent application by reference.

The present application relates to a dermatological treatment device comprising a laser head able to fire a laser beam. Such a device is typically used to create heating of a target zone comprising dermal tissues of a patient in order to accelerate healing thereof.

More particularly, the present invention relates to a protective sleeve able to protect the dermatological treatment device during use thereof, against any soiling. In connection with such soiling, the dermatological treatment device must be subject to strong sterilization in order to limit the risks of the transmission of pathogenic agents. Now, such sterilization would cause alterations of the device. Therefore, and in order to limit health risks and damage of the device, a protective sleeve is used that is able to be sterilized or, advantageously, intended for a single use. In this way, the risks of contamination are limited, without compromising the longevity of the treatment device itself.

The concept of such a protective sleeve is known in the field. In the case at hand, the sleeve according to the invention comprises a rigid shell and a flexible skirt; the flexible skirt being assembled on the edge of the rigid shell. Together, the rigid shell and the flexible skirt form an enclosure surrounding the dermatological treatment device. The rigid shell is configured so that it can be placed on the laser head and comprises a window, able to be arranged across from the laser beam, in order to allow the beam to traverse the sleeve from the device toward the outside in order to allow the beam to target the target zone of the skin to be treated and thus to perform the treatment. The rigid shell also comprises a contact wall arranged around the window. This contact wall is able, by its outer surface, to contact the patient's skin, around the target zone, in order to allow the beam to target the target zone. Furthermore, the contact wall provides preparation of the target zone, by stretching the skin at the target zone.

The efficacy and non-vulnerability of the treatment require precise and repeatable positioning, in terms of distance and orientation, of the laser beam relative to the target zone. This positioning can be obtained using the contact wall, supported by the sleeve, and precise positioning of the sleeve relative to the laser head and the laser beam.

The sleeves of the prior art do not perform this precise positioning function correctly, primarily due to the means for attaching the sleeve on the treatment device, which are missing or not effective enough in immobilizing the sleeve relative to the treatment device.

The present invention proposes an improved sleeve that avoids this drawback.

The invention relates to a protective sleeve for a dermatological treatment device comprising a laser head able to fire a laser beam, the sleeve comprising a rigid shell configured so as to be able to be placed on the laser head and comprising a window able to be arranged across from the laser beam, a contact wall, arranged around the window, able to come into contact around a target zone, and means for attachment to the device, where the attachment means is positioned as close as possible to the contact wall.

Advantageously, the attachment means is positioned less than 10 mm from the contact wall, preferably less than 5 mm.

According to another feature, the attachment means comprises at least one protuberance, able to be housed in a complementary cavity of the device, respectively a cavity able to accommodate a complementary protuberance of the device, preferably at least three protuberances and/or cavities.

According to another feature, said protuberances and/or cavities are angularly evenly distributed.

According to another feature, the window further comprises a border, arranged over the entire periphery of the window, substantially perpendicular to the contact wall and extending toward the inside of the sleeve.

The inventors have in fact noted that such a border made it possible, by contributing to stiffening the shell despite the opening formed at its window, to maintain the flatness of the wall coming into contact around the target zone and, in this way, the precise positioning of the laser head across from the target zone.

Additionally, the presence of such a border makes it possible, when the contact wall is pressed forcibly sometimes, to avoid injuring the patient with the edge of the window.

According to another feature, the extension of the border is comprised between 1 and 5 mm, preferably equal to 3 mm.

According to another feature, the window further comprises a ring, extending the border, positioned substantially perpendicular to the border and extending toward the inside of the window.

The inventors have also noted, with the integration of such a ring in addition to the border, that aside from obtaining still further improved stiffening of the shell, this ring made it possible to better protect the laser head from soiling from the patient. As a result, the dermatological treatment device required less drastic decontamination between two treatments and therefore had an improved lifetime.

According to another feature, the extension of the ring is comprised between 0.5 and 4 mm, preferably between 2 and 2.2 mm.

According to another feature, the window is oblong.

The inventors have in fact noted that such a shape, due to the absence of corners, limited injuries to the patient, and simultaneously did not interfere with the laser beam while imparting good stiffness to the assembly.

According to another feature, the window has a large axis at least equal to 23.75 mm and a small axis at least equal to 10.05 mm.

According to another feature, the sleeve further comprises a flexible skirt secured to the rigid shell and configured so as to form, with the rigid shell, an enclosure surrounding the device, where the flexible skirt comprises at least one ventilation opening.

Other features, details and advantages of the invention will emerge more clearly from the detailed description provided below for information in relation to the drawings, in which:

FIGS. 1-4 show one preferred embodiment of a rigid shell of a protective sleeve.

Figure 5:
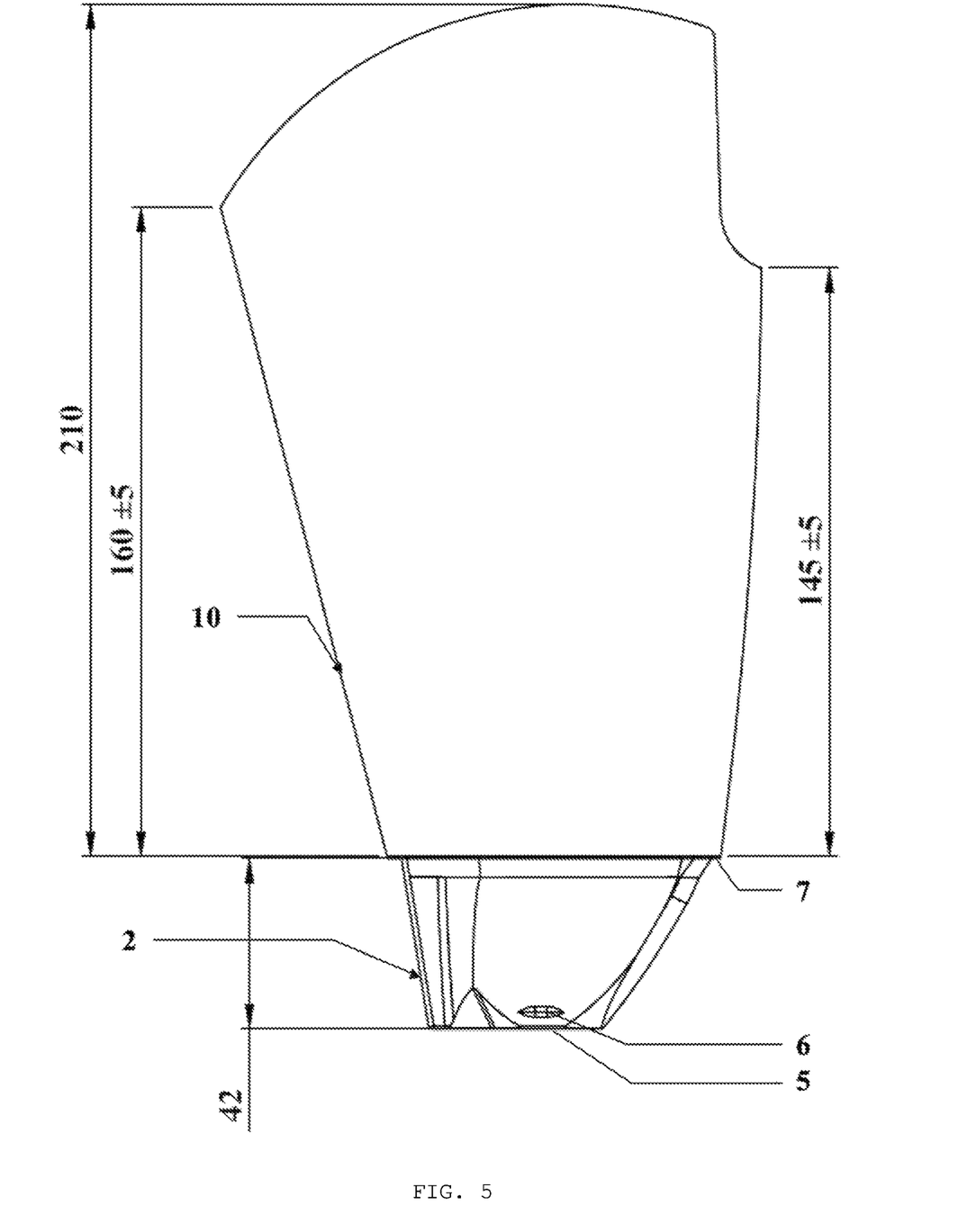
FIG. 5 shows a side view of the sleeve assembly with its rigid shell and its flexible skirt.
Figure 6:
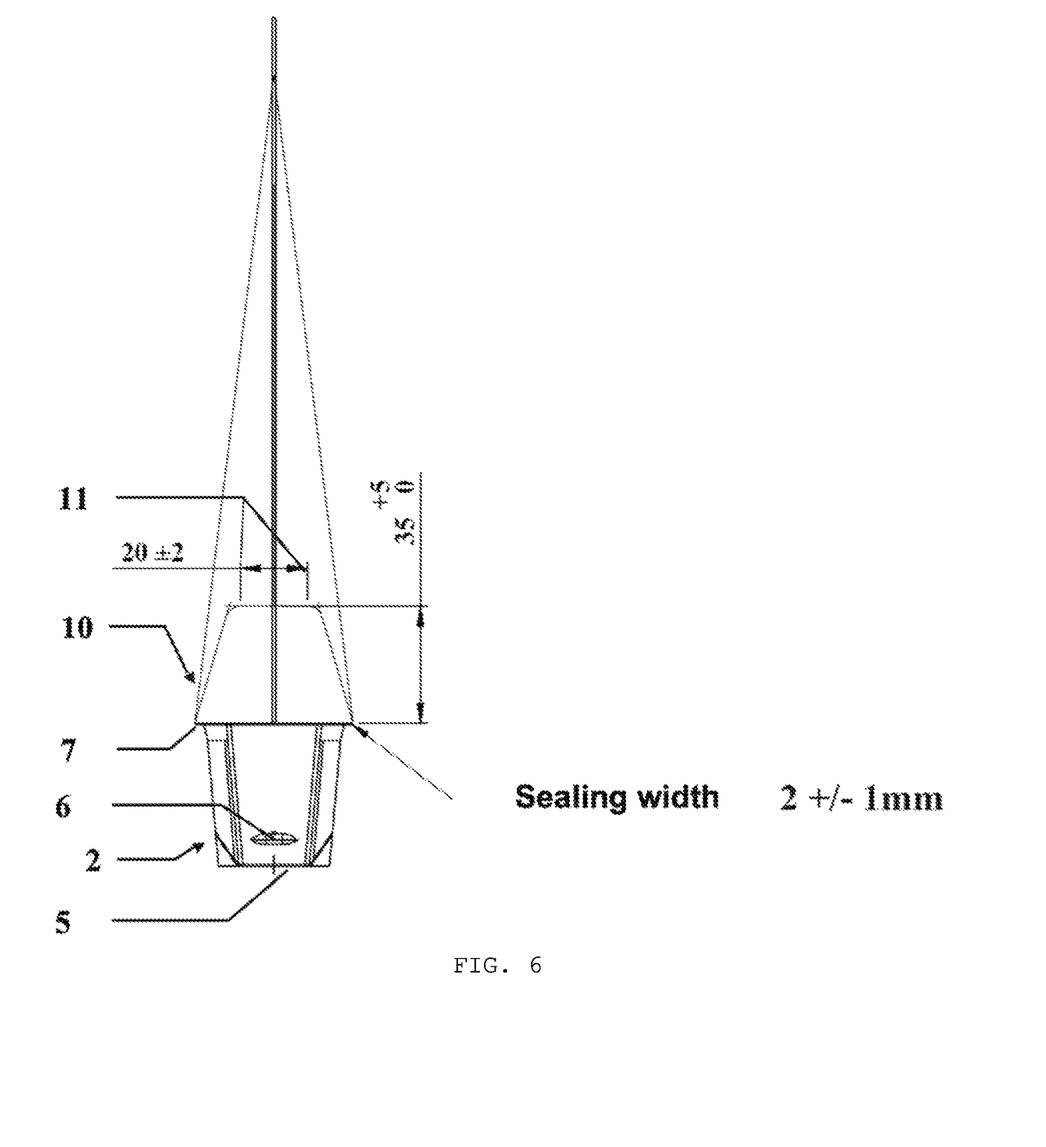
FIG. 6 shows a top view of this same sleeve assembly.

FIGS. 1-4 show a rigid shell 2 of the protective sleeve 1 for a dermatological treatment device. FIGS. 5-6 show a protective sleeve 1 with its rigid shell 2 and its flexible skirt 10. The dermatological treatment device (not shown) comprises a laser head able to fire a laser beam. One example of such a dermatological treatment device is given by European patent EP 2,519,176. The rigid shell 2 is able to cover the laser head. The rigid shell is advantageously made from a rigid plastic material, such as rigid PVC, PMMA (polymethyl methacrylate), polystyrene or fluorinated polymer. This makes it possible to perform the expected functions for a low cost, making it possible for the rigid shell 2 to remain disposable. The material of the shell may also contain one or several protective filters, preventing the reflection of the laser radiation. The shell is preferably transparent or translucent in order to facilitate, on the one hand, the placement of the sleeve on the dermatological treatment device and, on the other hand, the use of said device. The shell is preferably without openings, which makes it possible to avoid reflection of the laser beam toward the user or the patient. This also makes it possible to avoid soiling of the treatment device. The flexible skirt 10 covers the rest of the treatment device and is made from thin plastic film, which is preferably transparent or translucent. As an example, the latter can be made from polyurethane or flexible PVC. In order to form the protective sleeve 1, the flexible skirt 10 and the rigid shell 2 are sealed using well-known techniques, by gluing or hot welding, for example.

The sleeve 1 must not hinder the laser beam. Therefore, the sleeve 1 comprises a window 4 cut into the rigid shell 2. This window 4 is configured so as to be positioned across from the laser beam, advantageously centered and perpendicular relative to the laser beam, when the rigid shell 2 is placed on the laser head of the device. The window 4 is a cutout in the rigid shell 2 and does not contain any material, so as not to risk attenuating, reflecting or deflecting the laser beam.

The rigid shell 2 further comprises a contact wall 5. This contact wall 5 is positioned around the window 4, and is able to come into contact around the target zone. This contact wall 5 has any shape, preferably adapted to the device, for example flat, like in the illustrated embodiment. This contact wall 5 has at least two functions. A first function is a preparation function of the target zone, for example by performing smoothing or stretching of the skin. A second function is a positioning, both in terms of orientation and distance, of the laser beam relative to the target zone. For that, the contact wall 5 is advantageously substantially perpendicular to the laser beam, once the rigid shell 2 is immobilized relative to the laser head and the laser beam.

In order to perform this immobilization effectively, the rigid shell 2 further comprises an attachment means 6, allowing attachment of the rigid shell 2 with the treatment device, for example at the laser head.

Some sleeves of the prior art do not include attachment means and perform positioning of the laser beam relative to the target zone using contact of a contact face present on the laser head on the inner surface of the contact wall of the rigid shell. Such stacking is not effective to guarantee a constant distance from the target zone, much less a constant orientation.

Other sleeves of the prior art include an attachment means, located near the edge 7 of the rigid shell 2 of the sleeve 1. Such a location of the attachment means allows a deformation of the rigid shell between the attachment means and the contact wall. Consequently, a constant orientation and/or a constant distance of the laser beam relative to the target zone is not guaranteed.

According to one important feature of the invention, the attachment means 6 is positioned very close to the contact wall 5. Thus, in the embodiment illustrated in FIGS. 1-6, the attachment means 6, which comprises three clips, is positioned on the return walls of the contact wall 5, as close as possible to the contact wall 5, or as close as possible to the corner between the return wall and the contact wall 5 as allowed by the production constraints of the sleeve 1. In addition to the attachment means located close to the contact wall (proximal means), it is further possible to consider attachment means at a distance from the contact wall (distal means). In general, the attachment means can be concave or convex.

Thus positioned, the attachment means 6 guarantees an immobilization of the rigid shell 2 and the sleeve 1 in general relative to the laser head, such that the distance between the attachment means 6 and the contact wall 5, which may optionally allow a deformation, is extremely small. This guarantees an ideal positioning of the laser beam relative to the contact wall 5 and therefore relative to the target zone.

Advantageously, the attachment means 6 is such that it guarantees a unique position of the sleeve 1 relative to the device, thus ensuring repeatability of the treatment method. The rigid shell 2 is most often configured to substantially reproduce the shape of the laser head that it covers, such that the rigid shell 2 marries the laser head.

In the illustrated embodiment, the positioning of the attachment means 6 only allows a single positioning of the rigid shell 2 on the laser head. The non-revolutional shape of the laser head and the rigid shell 2 provides mistake-proofing in terms of rotation. There is thus a single position in which the rigid shell 2 can be positioned and attached on the laser head of the treatment device. This also guarantees that the window 4 is positioned correctly and oriented across from the laser beam.

According to one embodiment, as illustrated, the attachment means 6 comprises at least one protuberance 6. This protuberance 6 is configured and sized so as to be able to be housed in a complementary cavity (not shown) made in the device, typically at the laser head, and arranged opposite it. Preferably, the protuberance is ovoid. During the placement of the rigid shell 2 on the device, the elasticity of the rigid shell 2 can be taken advantage of in order to separate the protuberance 6 slightly during the approach of the cavity, to next allow it to return to the idle position, when the protuberance 6 engages in the cavity. This elasticity then ensures maintenance of the protuberance 6 in the cavity. The protuberance 6 makes it possible, by cooperating with the cavity, to perform clipping ensuring fastening of the rigid shell 2 on the device. This clipping is reversible and makes it possible to remove the sleeve 1 after use. A new sleeve can be installed for each new patient.

Alternatively, but equivalently, the attachment means may comprise a cavity (not shown) able to accommodate a complementary protuberance of the device.

The shell may also have guide means, in the form of a slot, for example, in order to facilitate the positioning of the sleeve on the treatment device.

It is also possible to consider means facilitating the removal of the sleeve. These means may assume the form of a recess or a border at the shell.

These embodiments may be combined, by mixing the cavities and/or the protuberances.

A single cavity/protuberance pair may suffice to produce an attachment means 6. However, the number of cavity/protuberance pairs can be increased. A preferred number of three pairs of protuberances and/or cavities is advantageous, in that it guarantees mechanically precise and repeatable positioning of the rigid shell 2 relative to the device. A larger number, although practically static, makes it possible to increase the holding or rigidity of the attachment.

Figure 1:
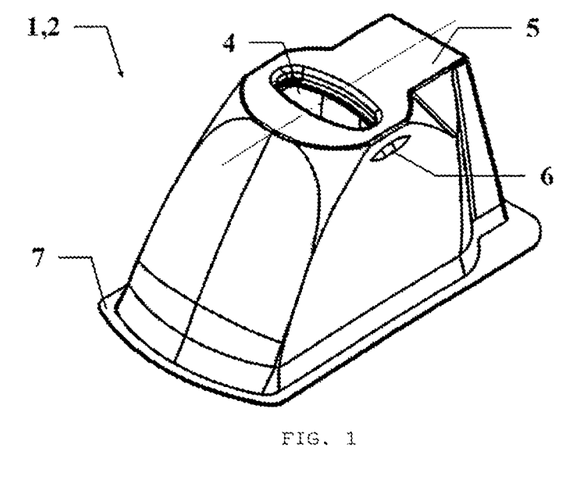
FIG. 1 shows a perspective view of the rigid shell.
Figure 2:
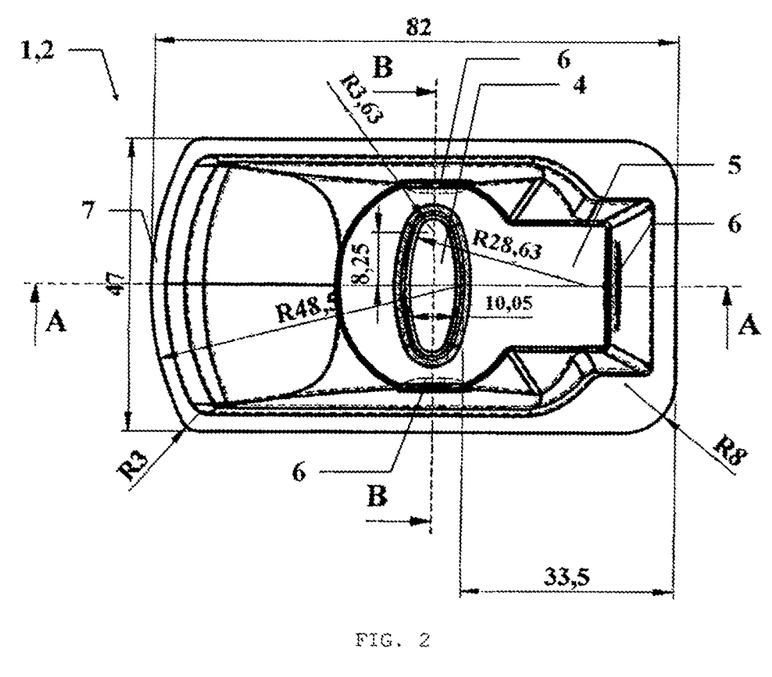
FIG. 2 shows a front view of this same shell.
Figure 3:
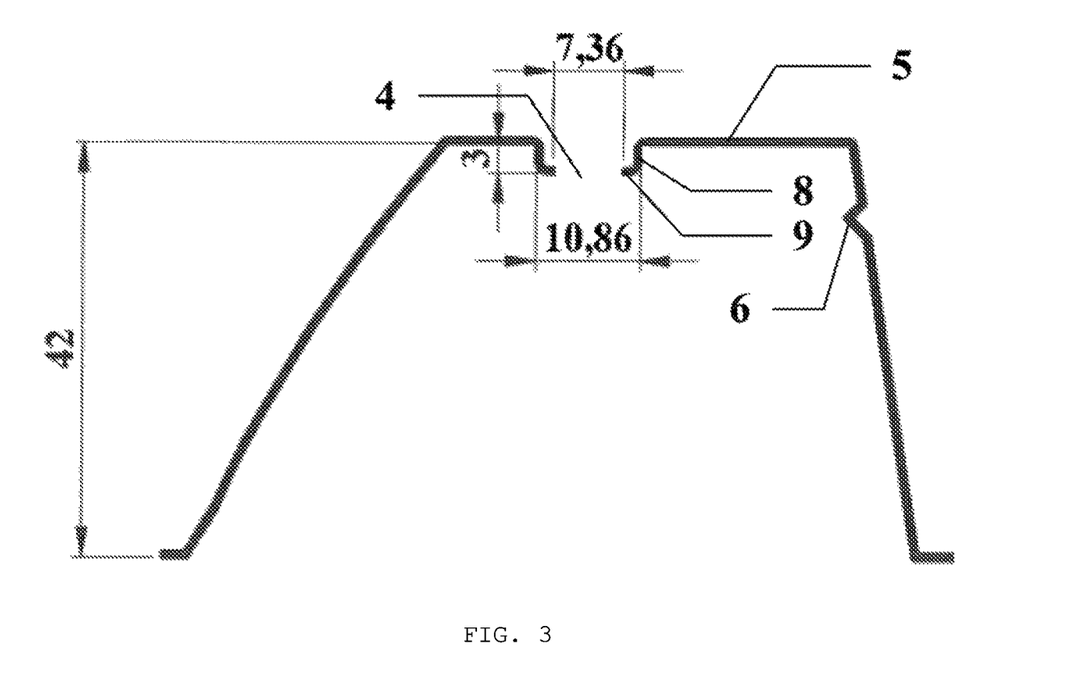
FIG. 3 shows a bottom view of the rigid shell cut along AA.
Figure 4:
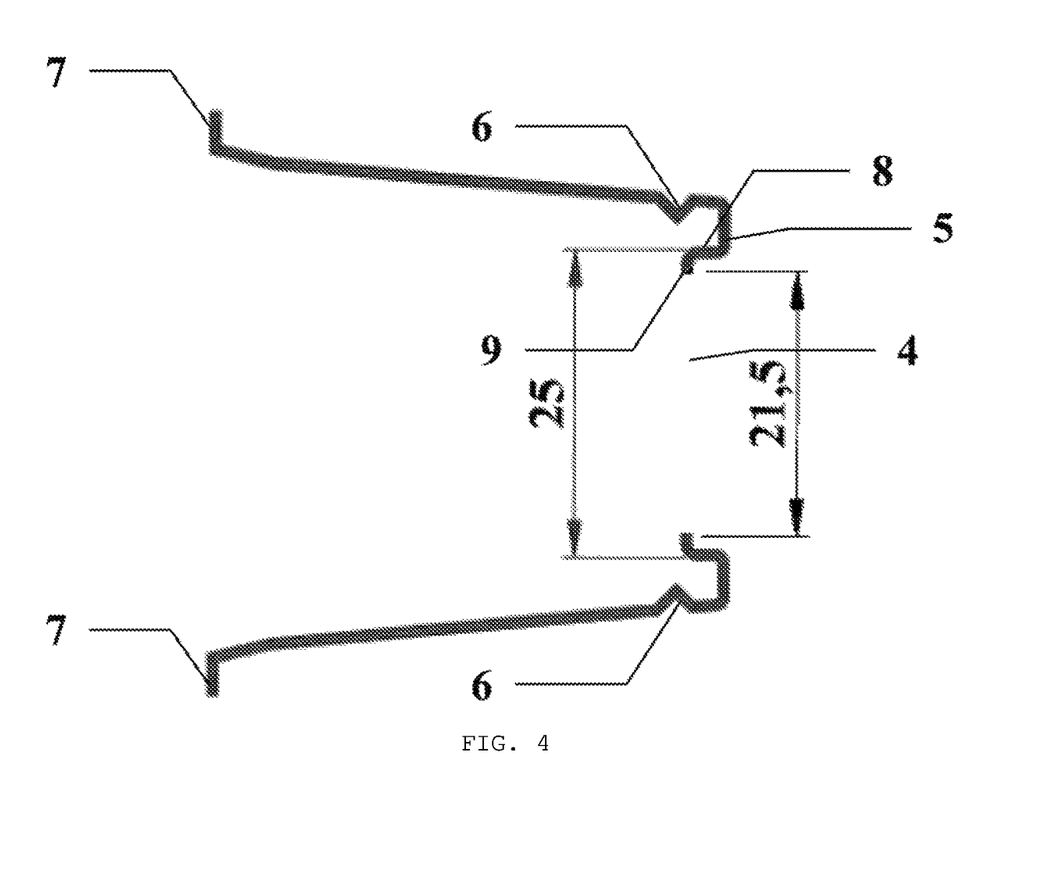
FIG. 4 shows a side view of the rigid shell cut along BB.

In the embodiment illustrated in FIGS. 1-6, three protuberances 6 are made in the rigid shell 2. A first protuberance 6, more particularly visible in FIG. 3, is arranged on the right lateral face of the rigid shell 2. Two other opposite protuberances 6, substantially parallel to one another and perpendicular to the previous one, are respectively positioned on the upper face and the lower face. They are particularly visible in FIGS. 1 and 4. The three protuberances 6 are simultaneously visible in FIG. 2.

According to one advantageous embodiment, in order to distribute the stresses and see to the relative positioning of the rigid shell 2 with respect to the device, said protuberances 6 and/or cavities are advantageously substantially evenly angularly distributed.

Another problem caused by the sleeves according to the prior art appears at the window 4. The window must allow the different beams to pass, including the laser beam, without risk of deflecting it, attenuating it or reflecting it. Therefore, the window 4 is a cutout formed in the rigid shell 2. The window 4 thus constitutes an opening at which the device is not protected and by which any soiling from the patient, such as blood, which may be a contaminant, can pass during the treatment to reach the device.

Relative to the prior art where the window is a simple cutout in the contact wall, the invention corrects this drawback. According to one feature of the invention, the profile of the window 4 of the shell 2 is modified in order to reduce or eliminate this risk of contamination.

To that end, the window 4 further comprises a border 8, positioned over the entire periphery of the window 4, substantially perpendicular to the contact wall 5 and extending toward the inside of the sleeve 1. Such a border 8 is more particularly visible in FIGS. 3 and 4. This border 8 thus reenters toward the inside of the sleeve 1 and toward the device in order to better protect against any soiling, if applicable by re-entering into a cavity of the laser head. Such a border 8 can be used alone, without the ring 9.

A border 8 has a substantially constant extension along the perimeter of the window 4. This extension is typically comprised between 1 and 5 mm. It is preferably equal to 3 mm.

Advantageously, in order to still further improve the protection of the device against soiling, the window 4 also comprises a ring 9. This ring 9 extends the preceding border 8. The ring 9 is arranged substantially perpendicular to the border 8 and extends inward/toward the center of the window 4. Such a ring 9 is particularly visible in FIGS. 3 and 4. It emerges from the preceding constructions that the ring 9 is substantially parallel to the contact wall 5. This makes it possible to form a screen parallel to and separated from the target zone. The distance makes it possible to avoid soiling by contact. The ring 9, thus separated from the contact wall 5 by the border 8, makes it possible to separate the window 4 from the target zone, which may be contaminating. The wall of the ring 9, however, provides protection against any projections.

A ring 9 has an extension typically comprised between 0.5 and 4 mm. This extension is preferably between 2 and 2.2 mm.

It goes without saying that the size of the window 4, as part cut into the rigid shell 2, remains identical, in that it is determined by the constraints related to the passage of the laser beam. Thus, the ring 9 is not deducted from the window 4. On the contrary, the presence of the ring 9 requires a discontinuity in the contact wall 5, increased by the size of the ring 9.

The laser beam used has a substantially rectangular shape. In no case may the laser beam interfere with one of the contours of the window 4. Therefore, the window 4 should have a cutout encompassing at least this rectangular shape. The rigid shell 2 is typically made by thermoforming for the body, with subsequent reworking of the cutout to produce the window 4. The positioning allowance during the cutout operation requires increasing the size of the window 4.

According to one obvious embodiment, used in the prior art, the window is sized according to a rectangle reproducing the rectangular shape of the laser beam, homothetically increased over all of its dimensions, by the allowance of the cutout operation, leading to a rectangle with larger dimensions.

Such a shape leads, however, to removing much more material from the contact wall 5, which may make it more fragile. Furthermore, the corners of said rectangular shape creates rupture onsets, further increasing the embrittlement.

Therefore, according to one feature of the invention, the shape of the window 4 is oblong.

According to one embodiment, this oblong shape is determined so as to satisfy two constraints. On the one hand, the oblong shape is such that it circumscribes the rectangle of the laser beam. On the other hand, the oblong shape is such that its dimensions along the small and large axes are equal to the dimensions of the laser beam increased by the allowance of the cutout operation. As a result, the oblong shape thus makes it possible to accommodate the rectangular shape of the laser beam while authorizing an offset of the window 4 caused by a misalignment during the cutout operation, at least along the axes of the oblong shape. This advantageously makes it possible to produce a less notched window 4, in that it does not comprise the corners cut out of a rectangle. Such a window 4 imparts better strength to the contact wall 5. This oblong shape with rounded corners and without direct cutouts in the plane with the skin of the patient avoids any injurious cuts for the patient.

For information in the illustrated embodiment, the laser beam has a size of 20×4 mm. The allowance of the cutout operation is typically +/−1.5 mm, broken down into +/−1 mm for the operation strictly speaking and +/−0.5 mm of general allowance over the overall dimensions. This leads, according to the prior art, to a rectangular window of 27×9 mm. On the contrary, according to the invention, an oblong window 4 has a large axis at least equal to 23.25 mm and a small axis at least equal to 10.05 mm.

The sleeve 1 typically comprises a rigid shell 2 for the functions requiring rigidity, like those previously seen for positioning, orientation and distance, of the laser beam relative to the target zone.

This rigid shell 2 makes it possible to partially surround a portable and mobile part of the device, called handheld part. The sleeve 1 further comprises a flexible skirt 10, secured to the rigid shell 2, typically welded at the edge 7. This flexible skirt 7 is typically made from flexible PVC.

This flexible skirt 10 is configured so as to complete, with the rigid shell 2, an enclosure surrounding the device. This enclosure surrounds the device and the sleeve 1 requires at least one ventilation opening 11. The necessary opening formed by the window 4 is not sufficient for effective ventilation. According to the prior art, such a ventilation opening 11 is arranged in the rigid shell. This is detrimental in that such an opening affects the mechanical strength of the rigid shell.

Therefore, according to another feature of the invention, the ventilation opening(s) 11 are advantageously arranged in the flexible skirt. This has the advantage of being able to eliminate the ventilation openings formed in the rigid shell 2, thereby increasing its strength. Another advantage lies in facilitating the operation for producing ventilation openings, the material of the flexible skirt being easier to cut.

The sleeve is preferably packaged with the skirt in a kit so as to facilitate its placement on the treatment device at the time of use.

Preferably, the sleeve is packaged in a carton and sterilized.

The invention claimed is:

1. A protective sleeve able to protect a dermatological treatment device comprising a laser head able to fire a laser beam during its use against any soiling, the sleeve comprising:
    a) a rigid shell configured so as to be able to be placed on the laser head and comprising:
       a window able to be arranged across from the laser beam,
       a contact wall, arranged around the window, able to come into contact around a target zone,
       means for attachment to the device positioned less than 10 mm, preferably less than 5 mm, from the contact wall, in the form of at least one protuberance, able to be housed in a complementary cavity of the device, said protuberance making it possible to perform reversible clipping on the device by cooperating with its cavity ensuring fastening of the rigid shell on the device and the removal of the sleeve after its use; and
    b) a flexible skirt secured to the rigid shell and configured so as to form, with the rigid shell, an enclosure surrounding the device.

2. The sleeve according to claim 1, where the attachment means comprises at least at least three protuberances and/or cavities.

3. The sleeve according to claim 2, where said protuberances and/or cavities are angularly evenly distributed.

4. The sleeve according to claim 1, where the window further comprises a border, arranged over the entire periphery of the window, substantially perpendicular to the contact wall and extending toward the inside of the sleeve.

5. The sleeve according to claim 4, where the extension of the border is comprised between 1 and 5 mm.

6. The sleeve according to claim 1, where the window further comprises a ring, extending the border, positioned substantially perpendicular to the border and extending toward the inside of the window.

7. The sleeve according to claim 6, where the extension of the ring is comprised between 0.5 and 4 mm.

8. The sleeve according to claim 1, wherein the window is oblong.

9. The sleeve according to claim 8, wherein the window has a large axis at least equal to 23.75 mm and a small axis at least equal to 10.05 mm.

10. The sleeve according to claim 1, wherein the flexible skirt comprises at least one ventilation opening.

11. The sleeve according to claim 1, wherein the window is a cutout in the rigid shell (2), thus not containing any material, so as not to risk attenuating, reflecting or deflecting the laser beam, and which comprises a border, arranged over the entire periphery of the window, substantially perpendicular to the contact wall and extending toward the inside of the sleeve.

12. The sleeve according to claim 1, wherein the contact wall (5) is substantially perpendicular to the laser beam once the rigid shell is immobilized relative to the laser head and the laser beam.

13. The sleeve according to claim 1, wherein the rigid shell covers the rest of the treatment device and is made from a rigid plastic material.

14. The sleeve according to claim 1, wherein the flexible skirt covers the rest of the treatment device and is made from thin plastic film, which is preferably transparent or translucent.

15. The sleeve according to claim 1, wherein said sleeve is intended for a single use.

16. The sleeve according to claim 1, further comprising means facilitating the removal of the sleeve, for example a recess or a border at the shell.

17. The sleeve according to claim 1, wherein the rigid shell is configured to substantially reproduce the shape of the laser head that it covers, such that the rigid shell marries the laser head.

* * * * *